United States Patent [19]

DeWitt et al.

[11] 4,029,085

[45] June 14, 1977

[54] METHOD FOR DETERMINING BILIRUBIN CONCENTRATION FROM SKIN REFLECTANCE

[75] Inventors: David P. DeWitt; Robert E. Hannemann, both of West Lafayette, Ind.; John F. Wiechel, Houston, Tex.

[73] Assignee: Purdue Research Foundation, West Lafayette, Ind.

[22] Filed: Mar. 26, 1976

[21] Appl. No.: 670,838

[52] U.S. Cl. .............................. 128/2 R; 128/2 G
[51] Int. Cl.² ........................................ A61B 5/00
[58] Field of Search ............ 128/2 R, 2 A, 2 L, 2 G

[56] References Cited
UNITED STATES PATENTS

| | | | |
|---|---|---|---|
| 2,437,916 | 3/1948 | Greenwald | 128/2 R |
| 3,811,777 | 5/1974 | Chance | 128/2 L X |
| 3,825,342 | 7/1974 | Lubbers et al. | 128/2 L X |

*Primary Examiner*—Kyle L. Howell
*Attorney, Agent, or Firm*—John R. Nesbitt

[57] ABSTRACT

A method is disclosed for determining the bilirubin concentration in the blood serum of a person from measurement of the spectral reflectance of the skin. The disclosed method detects the severity of jaundice, a common neonatal condition, and enables determination of the type of treatment regimen needed to prevent the bilirubin level from becoming sufficiently high to cause kernicterus which can result in brain damage. The method includes measuring the reflectance of the skin within a predetermined frequency spectrum, and more particularly at a number of specific wavelengths in the visible portion of the spectrum.

13 Claims, 4 Drawing Figures

METHOD FOR DETERMINING BILIRUBIN CONCENTRATION FROM SKIN REFLECTANCE

FIELD OF THE INVENTION

This invention relates to a method for detecting jaundice and establishing the level of severity by direct determination of the bilirubin concentration in the blood serum from measurement of the spectral reflectance of the skin at selected wavelengths.

BACKGROUND OF THE INVENTION

Jaundice, as is well known, is a condition one of the characterizations of which is yellowness of the skin of a person and is due to deposition of bile pigment resulting from excess bilirubin, known as hyperbilirubinemia, in the blood.

Bilirubin, in its indirect form, is potentially harmful, for example, to the central nervous system of a newborn infant. The severity of the damage caused is related to the level of bilirubin in the serum of the blood. In its most severe form, this damage is called kernicterus. After jaundice has been detected, treatment regimens, such as exchange transfusions and phototherapy, are commonly used, when considered necessary, to prevent levels of bilirubin known to cause kernicterus. It is currently felt that lower levels of bilirubin may also be one of the causes for minimal brain dysfunction, a condition thought to be responsible for a large majority of learning disorders in children. If such a relationship is true, early detection and treatment of lower level hyperbilirubinemia becomes even more critical.

The practice now commonly utilized in hospital nurseries for detecting jaundice is visual. A positive diagnosis is then normally verified by a serum bilirubin test using established laboratory techniques. While these techniques provide a reasonable indication of an infant's potential for kernicterus in most cases, the techniques now utilized have been shown to be inadequate in at least some instances, such as, for example, in the occasional development of kernicterus in infants with lower bilirubin levels (under 10 mg/100 ml).

The disadvantages of the current visual detection practice and laboratory confirmation process include the danger of missing many lower-level hyperbilirubinemias, causing a delay in the initiation of treatment until the laboratory results are known, causing discomfort to the infant, risking infection to the infant from the blood sample withdrawal process, being relatively expensive, and/or being time consuming and unsuited for mass screening.

Three factors must be normally considered in the visual detection process: experience of the physician or nursing staff, skin pigmentation of the infant, and nature of the environmental lighting of the nursery or hospital environment. Only the experienced nurse or medical practitioner can now consistently indentify the onset of jaundice.

In addition to the initial detection process, proper monitoring of bilirubin level during treatment for jaundice is likewise important. Improper monitoring can result in excessive or insufficient phototherapy or unintended delay in administering an exchange transfusion. Both initial detection of jaundice and the monitoring of jaundice during therapy are therefore critical in the treatment of the disorder.

Thus, the process of detecting jaundice in current nursery practice is based upon one vital sign — subtle color change of the infant's skin. Obviously, if subjective judgment in recognizing a subtle color change can be replaced by a dependable quantitative apparatus and method to detect jaundice, this would provide a needed improvement.

SUMMARY OF THE INVENTION

This invention provides a method for detecting jaundice in a person utilizing a determination of bilirubin concentration from spectral reflectance measurements of the skin.

It is therefore an object of this invention to provide an improved method for detecting jaundice.

It is another object of this invention to provide a method for detecting jaundice by measuring spectral reflectance from the skin of a person.

It is another object of this invention to provide a method that measures the blood serum bilirubin concentration of a person with said measurement being in agreement with established procedures requiring blood samples which must be removed from the person's blood stream.

It is yet another object of this invention to provide a method for detecting jaundice by determining bilirubin concentration of a person in a noninvasive manner.

It is still another object of this invention to provide a method for quickly determining bilirubin concentration at the site of a patient.

It is another object of this invention to provide a method for determining bilirubin concentration of a patient without disturbance to the physical positioning of the patient.

It is yet another object of this invention to provide a method for determining bilirubin concentration of a patient without unnecessary constraint to the patient and during normal body movements.

It is another object of this invention to provide a method for detecting jaundice that is independent of the patient's skin pigmentation, spectral distribution of ambient lighting, and color of the patient's enclosure.

It is still another object of this invention to provide a method to detect the presence of jaundice that is quantitative rather than subjective.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the hereindisclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
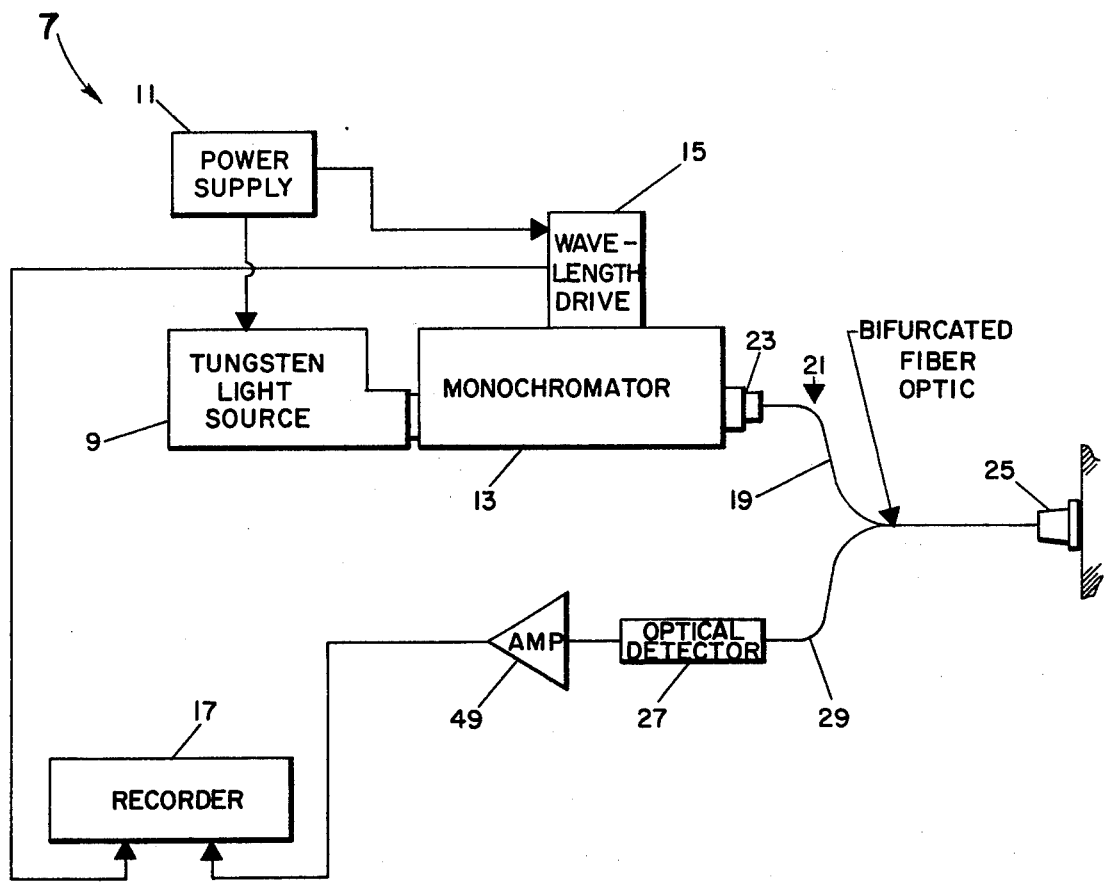
FIG. 1 is a block diagram of the apparatus of this invention showing the elements of a measuring system to obtain the spectral reflectivity of a patient's skin.

Referring now to the drawings, the spectral reflectivity of the patient's skin can be obtained by the apparatus, or system, 7 as shown in FIG. 1. A light source 9, typically a tunsten-halogen filament lamp, has power supplied thereto from a conventional power supply 11. Light source 9 is optically coupled to a dispersion device 13, such as a grating or prism type monochromator, which provides a resolved spectral band width, $\Delta\lambda$, of less than 10 nm. The wavelength band passed and the spectral scan rate are determined and controlled by wavelength drive mechanism 15 which is also connected to power supply 11.

Drive mechanism 15 also provides an electrical signal output to recording device 17 that is proportional to the wavelength of the spectral band, the proportionality being determined by conventional wavelength calibration procedures.

The spectral flux exiting from the dispersion device 13 is passed to the input leg 19 of a bifurcated fiber optic system 21 through an optical coupler 23 comprised of a conventional lens arrangement. The functions of the bifurcated fiber optical system 21 are to connect the spectral source with probe 25, which contacts the patient's skin, to allow motion of the probe 25 relative to the dispersion device 13 permitting ease of application to the patient in any position, and to connect probe 25 with optical detector 27 through output, or return, leg 29 of the bifurcated fiber optic system 21.

The bifurcated fiber optic system 21 (consisting of input leg 19 and output leg 29) transmits the spectral flux from the dispersion device to probe 25 and then is incident upon the patient's skin. Spectral flux reflected from the patient's skin reach the fiber optic elements of output leg 29 which are randomly arranged and gathered with the fibers from the input leg 19 at probe 25. The light reflected from the skin of the patient and collected at output leg 29 of the fiber optic system is then conducted from the probe through leg 29.

Figure 2:
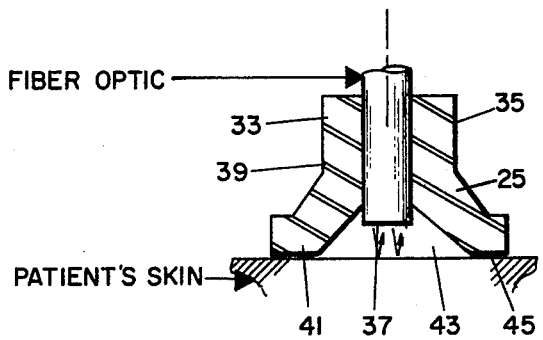
FIG. 2 is a sectional view of the probe shown in FIG. 1.

Probe 25, as indicated in FIG. 2, includes a housing 33 that is constructed from a material that is opaque to room ambient light in order to minimize stray radiation with the material being nonconducting to electrically isolate the patient from ground leakage and potential harm. Housing 33 is preferably generally cylindrical and includes a body portion 35 having an aperture therein to receive the free end 37 of bifurcated fiber optic system 21. End 37 of the fiber optic system may be maintained in the aperture in body portion 35 of the probe by frictional engagement between end 37 and body portion 35 or a bond may be established therebetween in conventional fashion, such as by use of an adhesive, if desired. The lower end 39 of probe 25 extends outwardly and downwardly from body portion 35 and terminates as annular ring 41. As shown in FIG. 2, this creates a generally conical space 43 below the lower end of body portion 35 of the probe that is surrounded by lower end 39 and ring 41. When ring 41 is then brought into contact with the skin 45 of a patient, the space 43 is enclosed for a better and more accurate light reflectance from the skin of the patient.

The end 37 of fiber optic system 21 within probe 12 is polished flat and positioned in such a manner that the end is either touching the skin or at a distance such as 1 to 3 mm above the plane of the skin. The precise location of the end of the fiber optic bundle 21 relative to the plane of the skin affects the magnitude of the spectral flux collected by output leg 29 of the fiber optice system but will have a minimal influence on the accuracy in determining the condition jaundice.

The flux reflected from the patient's skin is transmitted through the fiber optic system (through output leg 29) to the detection system consisting of optical detector 27 which provides an electrical signal proportional to the flux incident upon its active element. This electrical signal is coupled through amplifier 49 which provides a higher level signal to the recording device 17. Recording device 17 is a two-channel system to simultaneously record the wavelength position signal from the wavelength drive system 15 and the spectral reflected flux signal originating at probe 25 in contact with the patient's skin.

Included in the method of the invention is obtaining the ratio of the detector signal corresponding to the spectral flux reflected from the patient's skin to the detector signal corresponding to the spectral flux reflected from a perfectly diffusing reflecting standard, such as barium sulphate. The ratio of these signals is the true, or absolute, spectral reflectivity of the patient's skin and is independent of the spectral responsivity of the detector 27, spectral radiant power of the source 9, and optical transfer functions of the dispersion device 13, optical coupler 23, and the fiber optic system 21. Most important is that the ratio (or spectral reflectivity) is only slightly influenced by the configuration of the probe 25 and the spacing between the end 37 of fiber optic system 21 and the patient's skin.

Figure 3:
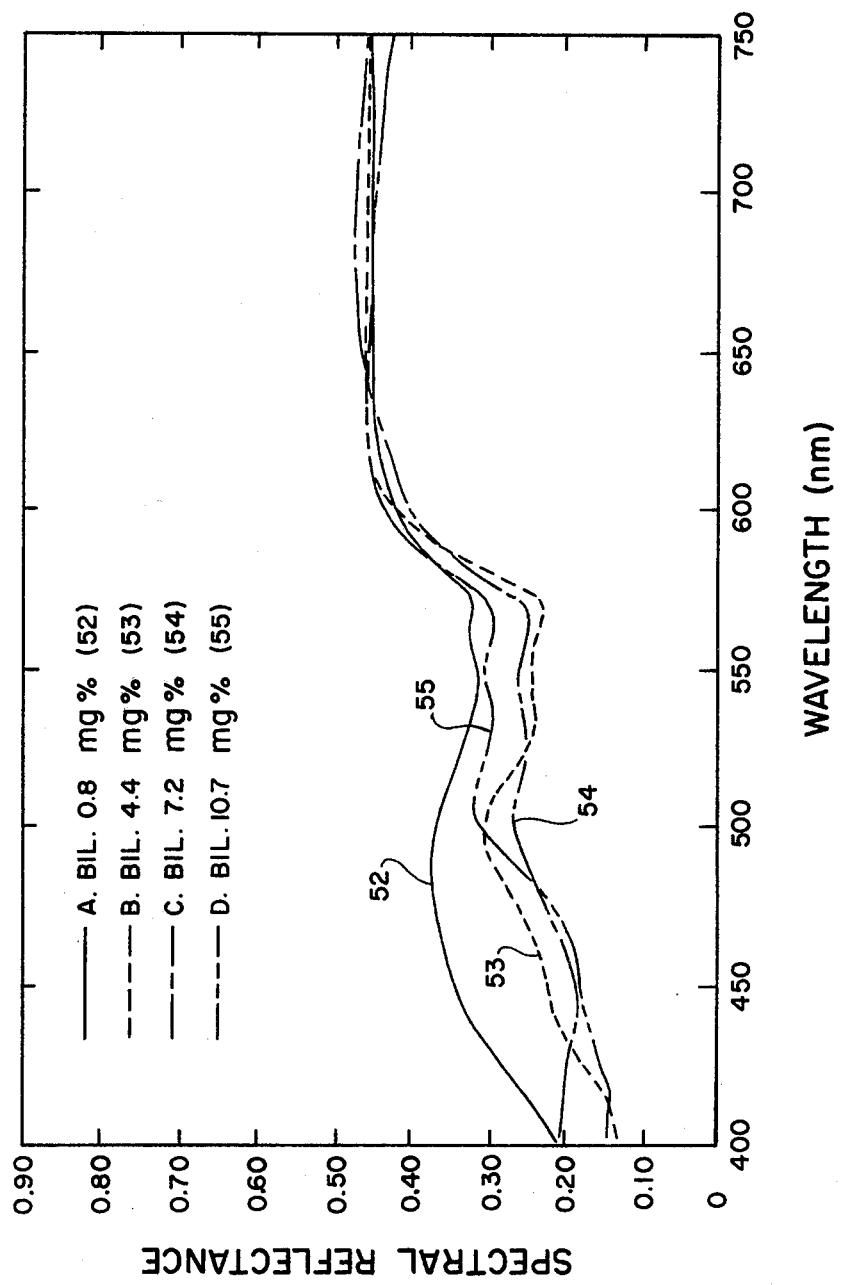
FIG. 3 is a graphical illustration of a typical skin reflectance spectra for patients with differing degrees of jaundice as indicated by bilirubin concentrations measured by the apparatus of FIG. 1.

FIG. 3 illustrates typical spectral reflectivity measurements made by apparatus 7 as shown in FIG. 1. The coordinates of this graph include wavelengths corresponding to the region of the visible spectrum in which the human skin displays spectral character and spectral reflectivity represented by the ratio of the spectral flux reflected from the patient's skin to that reflected from a perfectly diffusing reflecting standard. Four curves 52–55 are shown of patients having differing degrees of severity of jaundice as indicated by the level of bilirubin concentration in blood expressed in units of mg/100 m l of serum. It should be noticed that all the curves have the same general shape. It is not possible by inspection alone to relate changes in the spectral reflectance at any one wavelength or changes in the shape of the curves with the bilirubin concentration. The individuality of each patient's spectral reflectance due to pigmentation and textural characteristics needs to be considered before the bilirubin concentration can be related to the reflectance spectra.

The method of the invention to relate the reflectance spectra similar to those illustrated in FIG. 3 to the bilirubin concentration is based upon an analysis of variance. This analysis determines to what extent the level of the bilirubin concentration can be explained by some function or combination of skin spectral reflectance values at discrete wavelengths. Mathematically, this is expressed as $$BL = m + \sum_{i=1}^{j} n_i f(\rho_i)$$

where BL is the serum bilirubin concentration measured in mg bilirubin per 100 ml of serum, $m$ is a constant, $n_i$ and $f(\rho_i)$ are respectively coefficients of some function of the spectral reflectance at discrete wavelengths denoted by the subscript $i$, and $j$ is the number of such terms corresponding to $i$ wavelengths that are required. The nature of the function $f(\rho_i)$ can be linear, logarithmic, double logarithmic, or any other mathematical function which satisfies the analysis to the degree of confidence required.

The results of the analysis of variance on a sample population of 30 infants as shown in Table 1.

Table 1.

| Spectro-correlation Analysis of Data | | | | | |
|---|---|---|---|---|---|
| Analysis | Wavelength (nm) | | | | $R^2$ |
| First Order Linear | 450 | | | | .783 |
| Regression | 460 | | | | .776 |
|  | 420 | | | | .708 |
|  | 530 | | | | .193 |
|  | 550 | | | | .169 |
|  | 600 | | | | .064 |
| Multiple Linear | | 450 | | | .783 |
| Regression | | 450 | | 550 | .835 |
|  | | 450 | 530 | 550 | .868 |
|  | 410 | 450 | 530 | 550 | .882 |
|  | 410 | 440 | 450 | 530 | 550 | .915 |
| Polynomial Nonlinear | | 460 | | | .796 |
| Regression | | 460 | | 545 | .847 |
|  | 425 | 460 | | 545 | .884 |
|  | 425 | 460 | 535 | 545 | .922 |
|  | 425 | 460 | 525 | 535 | 545 | .931 |

The first column of Table 1 describes the nature of the mathemtatical function, the second column identifies the single wavelength or combination of wavelengths used in the analysis, and the third column is the coefficient of determination $R^2$. The $R^2$ value gives a statistical measure of the closeness of fit of the observed reflectance measurements to the mathematical relation. As can be seen from Table 1, simple linear relationships (first order linear regression) between spectral reflectivity at any one wavelength and bilirubin level give $R^2$ values too low to be of any practical use. The multiple linear regression considers 2, 3, 4, and 5 discrete wavelength combinations resulting in improved $R^2$ values. However, the highest $R^2$ value was obtained from a double logarithmic function involving the five wavelengths shown in the last line of Table 1.

Figure 4:
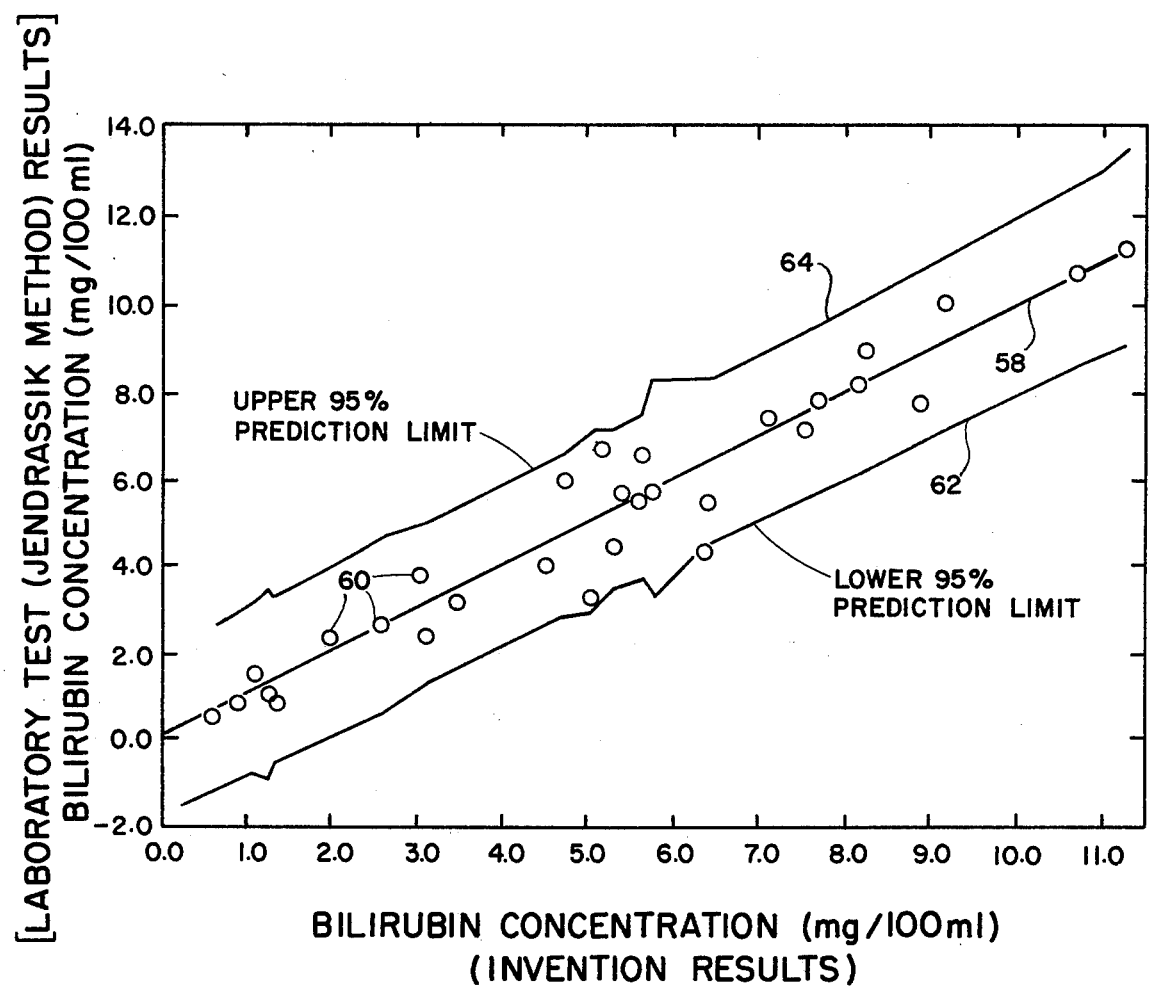
FIG. 4 is a graphical illustration of the comparison of bilirubin concentration measurements achieved utilizing this invention as compared with measurements by the Jendrassik method.

FIG. 4 illustrates the comparison bilirubin concentration results determined by the conventional laboratory chemical test with the bilirubin concentration result determined by the apparatus and method of this invention.

Curve 58 as shown in FIG. 4 is represented by the relationship, $$BL = m - \sum_{i=1}^{5} n_i \ln\ln(\rho_i)$$

where the function represented by the general expression above is known to be a double logarithmic function, $m = 14.40$, and the coefficients $n_i$ and the discrete wavelength denoted by the subscript $i$ are

| Wavelengths Corresponding to Subscript i (nm) | Coefficient, $n_i$ |
|---|---|
| 425 | −13.30 |
| 460 | −39.24 |
| 525 | −19.75 |
| 535 | −75.08 |
| 545 | +137.66 |

Thus, $$b = 14.40 - 13.30\ln\ln(\rho 425) + 39.24\ln\ln(\rho 460) \\ - 19.74\ln\ln(\rho 525) - 75.08\ln\ln(\rho 535) + 137.66\ln\ln(\rho 545)$$

where
 $b =$ serum bilirubin concentration measured in mg/100 ml of serum, and
 $\rho =$ spectral reflectance at wavelength $n$
with the measurement of the spectral reflectance skin at wavelengths 425, 460, 525, 535, and 545 nm, which wavelengths were not randomly selected but are physically related to the optical properties of individual constituents of the blood serum.

FIG. 4 illustrates the invention results by comparing the bilirubin concentration determined by the invention to the bilirubin concentration determined by conventional laboratory tests based upon the Jendrassik method. On the basis of measurements made on 30 infant patients represented by the open circles 60 on this graph of FIG. 4, the 95% confidence limits (represented by curves 62 and 64) indicate that the device and method of the invention can determine the bilirubin concentration with an accuracy of ±2 units over the region 0.5 to 10 mg/100 ml concentration using the specific relationship described above.

The apparatus and method of this invention are illustrated hereinabove, but the invention is not meant to be limited to the exact embodiment shown and described. The apparatus in its simplest form could be realized, for example, by an apparatus in which only the spectral reflectance or a parameter proportional to the spectral reflectance at the specific wavelengths identified above are measured. Such an apparatus could be constructed using dispersion devices other than a prism monochromator operating in other than a continuous wavelength scanning mode. In addition and again by way of example, specific relationship of a form different from the one described could be generated using the method of analysis of variance, other statistical and mathematical treatments, and/or physical modeling of the interaction of light with skin. The essential thrust of the apparatus and method of this invention is that the spectral reflectance of the skin of a jaundiced patient contains sufficient information from which the bilirubin concentration in the blood stream can be determined.

What is claimed is:
1. A method for detecting jaundice in a patient, said method comprising:
 measuring the spectral reflectance of the skin of a patient; and
 determining from said measured reflectance the bilirubin concentration in the blood of said patient.
2. The method of claim 1 wherein the method includes measuring the spectral reflectance of the skin of a patient by subjecting the skin to light emitted at a plurality of predetermined frequencies, collecting light reflected at each of said predetermined frequencies, and generating electrical signals the magnitude of each of which is proportional to said collected light reflected from said skin at said predetermined frequencies.

3. The method of claim 2 wherein said skin is subjected to light emitted at predetermined frequencies within a range of about 425 to 545 nm.

4. The method of claim 1 wherein said bilirubin concentration is determined from said measured reflectance utilizing the formula $$BL = m + \sum_{i=1}^{j} n_i f(\rho_i)$$

where BL is the serum bilirubin concentration measured in mg bilirubin per 100 ml of serum, $m$ is a constant, $n_i$ and $f(\rho_i)$ are respectively coefficients and some function of the spectral reflectance at discrete wavelengths denoted by the subscript $i$, and $j$ is the number of terms corresponding to $i$ wavelengths that are required.

5. The method of claim 4 wherein said number of terms utilized is a plural number.

6. The method of claim 5 wherein said number of terms utilized is 5 and wherein a double logarithmic function is utilized.

7. The method of claim 1 wherein said spectral reflectance is measured by noninvasively contacting the skin of a patient.

8. The method of claim 1 wherein the method includes determining a ratio based upon the reflectance of the skin of a patient and the reflectance from a standard.

9. The method of claim 2 wherein the method includes subjecting a predetermined standard to light waves at a plurality of predetermined frequencies, collecting light waves reflected from said standard, generating electrical signals proportional to said light waves reflected from said standard, and determining the ratio between said electrical signals reflected from the skin of a patient and the electrical signals reflected from said standard, said ratio being the true spectral reflectivity of the skin of a patient.

10. The method of claim 1 wherein said method is utilized to determine the level of severity of jaundice in a patient.

11. The method of claim 10 wherein said method is repeated at intervals to monitor the progress of the severity of jaundice in a patient.

12. A method for determining the bilirubin concentration in the blood of a person, said method comprising:
generating light at a plurality of frequencies;
directing said generated light at the skin of a person;
collecting light reflected from the skin of a person and generating therefrom electrical signals indicative of said reflected light that is collected; and
providing an indication of the bilirubin concentration of said person from the magnitude of said electrical signals produced.

13. The method of claim 12 wherein said method includes generating electrical signals based upon a predetermined standard, and determining the ratio between said electrical signals from the skin of a person and said electrical signals based upon said predetermined standard whereby the true spectral reflectivity of the skin of said person is established.

* * * * *